United States Patent
Bristow et al.

(10) Patent No.: US 10,499,639 B2
(45) Date of Patent: Dec. 10, 2019

(54) HERBICIDAL COMPOSITION, A METHOD FOR ITS PREPARATION AND THE USE THEREOF

(71) Applicant: JIANGSU ROTAM CHEMISTRY CO., LTD., Kiangsu (CN)

(72) Inventors: James Timothy Bristow, Chai Wan (HK); Yifan Wu, Chai Wan (HK)

(73) Assignee: JIANGSU ROTAM CHEMISTRY CO., LTD., Jiangsu (CN)

( * ) Notice: Subject to any disclaimer, the term of this patent is extended or adjusted under 35 U.S.C. 154(b) by 0 days.

(21) Appl. No.: 15/126,258

(22) PCT Filed: Mar. 6, 2015

(86) PCT No.: PCT/CN2015/073733
§ 371 (c)(1),
(2) Date: Sep. 14, 2016

(87) PCT Pub. No.: WO2015/143979
PCT Pub. Date: Oct. 1, 2015

(65) Prior Publication Data
US 2017/0079272 A1    Mar. 23, 2017

(30) Foreign Application Priority Data

Mar. 26, 2014 (GB) .................... 1405446.4

(51) Int. Cl.
*A01N 43/80* (2006.01)

(52) U.S. Cl.
CPC .................... *A01N 43/80* (2013.01)

(58) Field of Classification Search
CPC ........ A01N 43/80; A01N 25/04; A01N 25/22; A01N 25/28
See application file for complete search history.

(56) References Cited

U.S. PATENT DOCUMENTS

| | | | |
|---|---|---|---|
| 5,783,520 A | 7/1998 | Anderson et al. | |
| 6,380,133 B2 | 4/2002 | Becker et al. | |
| 2001/0041659 A1 | 11/2001 | Becker et al. | |
| 2007/0042182 A1* | 2/2007 | Markus | A01N 65/00 428/402.2 |
| 2009/0099024 A1* | 4/2009 | Casana Giner | A01N 25/28 504/301 |
| 2011/0269063 A1 | 11/2011 | Wu | |
| 2013/0095158 A1* | 4/2013 | Denuell | B01J 13/14 424/401 |
| 2014/0031231 A1 | 1/2014 | Liu et al. | |

FOREIGN PATENT DOCUMENTS

| | | | | |
|---|---|---|---|---|
| CN | 1162902 A | 10/1997 | | |
| CN | 1343092 A | 4/2002 | | |
| CN | 101507436 A | 8/2009 | | |
| CN | 101747187 A * | 6/2010 | | |
| CN | 101984808 A | 3/2011 | | |
| EP | 0792100 B1 | 1/2003 | | |
| EP | 1652433 A1 | 5/2006 | | |
| EP | 1640145 A1 | 10/2007 | | |
| WO | 0054590 | 5/1996 | | |
| WO | 9614743 A1 | 5/1996 | | |
| WO | 9824317 A1 | 6/1998 | | |
| WO | 0010392 A1 | 3/2000 | | |
| WO | 0054590 A1 | 9/2000 | | |
| WO | 2011121407 A1 | 10/2011 | | |
| WO | 2013021229 A1 | 2/2013 | | |
| WO | 2013105107 A2 | 7/2013 | | |
| WO | WO 2013105107 A2 * | 7/2013 | ............. | A01N 25/28 |
| WO | WO 2014018188 A1 * | 1/2014 | ............. | A01N 25/28 |

OTHER PUBLICATIONS

International Search Report from PCT/CN2015/073733 dated Jun. 2, 2015.
Written Opinion rom PCT/CN2015/073733 dated May 26, 2015.
GB Search Report for Application No. GB1405446.4 dated May 24, 2014.
French Office Action regarding 1552157 filed Mar. 17, 2015.
Chinese Office Action from corresponding Application No. CN201580003717.4 dated Mar. 21, 2019.
Indian Examination Report from corresponding IN Application No. 201627027200 dated May 17, 2019.
Extended European Search Report regarding European Application No. 15 76 8386.3 dated Aug. 17, 2017.
European Search Report regarding European Application No. 15 768 3863 dated Dec. 14, 2018.

* cited by examiner

*Primary Examiner* — Sue X Liu
*Assistant Examiner* — Nathan W Schlientz
(74) *Attorney, Agent, or Firm* — Dickinson Wright PLLC

(57) ABSTRACT

A herbicidal composition comprising an aqueous suspension of microcapsules is provided. The microcapsules have a capsule wall of a porous condensate polymer, wherein the microcapsules contain a solution of clomazone in a solvent system comprising one or more non-edible oils. A method for preparing the composition comprises providing a water immiscible phase comprising clomazone, an isocyanate and optionally an ACD cross-linker, dissolved in a solvent system comprising a non-edible oil; providing an aqueous phase comprising one or more surfactants; combining the water immiscible phase and the aqueous phase to form a dispersion of the water immiscible phase in the aqueous phase; thereby forming microcapsules of polyurea containing droplets of the water immiscible phase; and curing the microcapsules.

29 Claims, No Drawings

HERBICIDAL COMPOSITION, A METHOD FOR ITS PREPARATION AND THE USE THEREOF

This application is a 371 national phase entry of PCT/CN2015/073733, filed 6 Mar. 2015, which claims benefit of GB Patent Application No. 1405446.4, filed Mar. 26, 2014, the entire contents of which are incorporated herein by reference for all purposes.

FIELD OF THE INVENTION

The present invention relates to a herbicidal composition comprising clomazone as the active ingredient. The invention further relates to the preparation of the formulation and to its use.

BACKGROUND

Formulations of clomazone are known and are available commercially. One commercial formulation of clomazone is a solvent-based emulsifiable concentrate (EC). The formulation is typically prepared by dissolving the clomazone active ingredient in an inert organic liquid solvent, together with an appropriate emulsifier system. Mixing the resulting combination with water, spontaneously forms an oil in water emulsion of the clomazone/solvent solution.

Modern agricultural practice requires improved control in the application of biologically active components to the target plants. This improved control in turn provides for a number of advantages. First, the improved control of the active ingredient allows compounds to be used that have an increased stability over extended periods of time. Further, the improved control leads to a reduction in the environmental hazard presented by the herbicidal composition. In addition, improved control leads to a decrease in the acute toxicity of the composition and allows any incompatibility between ingredients to be accommodated.

It is known that microencapsulation is a technique that offers a number of advantages in improving the control achievable in the delivery of herbicidal formulations, compared with other formulation techniques in the field of agrochemicals. Several basic processes for the preparation of microencapsulation formulations of herbicidally active compounds have been disclosed and are known in the art. In particular, known techniques for microencapsulation include coacervation, interfacial polymerization and in-situ polymerization. Most commercially available CS (microcapsule suspension) formulations are manufactured by interfacial polymerization. Examples of commercial CS formulations prepared in this manner include Chlorpyrifos CS, Lambda-cyhalothrin CS, Fluorochloridone CS, and Methylparation CS. When such formulations are dried, they form water dispersible granules containing microcapsules, with the active ingredient being contained within the microcapsules. The microcapsules act to contain the active ingredient, such that when the formulation is applied, for example as a dispersion in water, the active ingredient is released slowly from the microcapsules and its spread outside the locus of application is limited.

Clomazone, (2-[(2-chlorophenyl)methyl]-4,4-dimethyl-3-isoxazolidinone) is a well-known herbicide for controlling soybean, cotton, cassava, corn, rapeseed, sugar cane, tobacco and other crops. It is known in the art to formulate clomazone by microencapsulation. However, due to the physical properties of clomazone, for example its high volatility, determining the optimum formulation is still highly demanding.

For example, U.S. Pat. No. 6,380,133 discloses a technique to encapsulate clomazone in microcapsules having a shell of a cross-linked polyurea. However, control of the release rate of clomazone is still not satisfactory.

One known method of preparing a CS formulation is by interfacial polymerization. In this method, the active ingredient is dissolved in a solvent, together with monomers and/or prepolymers. The resulting mixture is dispersed into a water phase containing one or more emulsifiers, optionally one or more protective colloids and, optionally, additional prepolymers. A capsule wall is formed around the oil droplets as a result of interfacial polymerization occurring at the oil/water interface in the presence of a catalyst or by heat.

Solvents, although generally inert in the finished formulation, are used in the microencapsulation of active ingredients to perform a number of roles, for example dissolving the active component to allow encapsulation of solid active ingredients, and adjusting the diffusion rate of the active substance through the polymeric wall, in turn aiding in controlling the release of the active ingredients from the microcapsules when the formulation has been applied. In addition, solvents may be selected, in addition to their role of dissolving the active components, to influence the emulsion quality, for example by maintaining a low viscosity during the emulsification and/or polymerization steps.

EP 1 652 433 describes a herbicidal formulation comprising an aqueous liquid composition having suspended therein a plurality of solid microcapsules, the microcapsules having a capsule wall of porous condensate polymer of at least one of a polyurea, polyamide or amide-urea copolymer. The microcapsules are formed to encapsulate clomazone as the active ingredient. Within the capsules, the clomazone is dissolved in a high boiling inert organic solvent, in particular a 1,2-benzenedicarboxylic di-($C_3$-$C_6$) branched alkyl ester.

EP 0 792 100 describes a process for preparing an encapsulated clomazone formulation. The process involves a step of providing a water immiscible liquid phase consisting of clomazone and polymethylene polyphenyl isocyanate, with or without an aromatic hydrocarbon solvent. EP 0 792 100 describes the microencapsulation of clomazone by preparing a water-immiscible phase containing specified amounts of clomazone and polymethylene polyphenyl isocyanate (PMPPI), together with an aromatic solvent. The solvent is indicated to be optional in the case of formulations with high loadings of clomazone. However, the exemplified formulations generally contain a petroleum solvent in an amount of from 4 to 6% by weight.

EP 1 840 145 discloses a microencapsulated formulation of clomazone, in which the clomazone is dissolved in a solvent, in particular cyclohexanone and retained with microcapsules having a shell formed from a polymer prepared by interfacial polymerization involving the reaction of an isocyanate with an acetylene carbamide derivative.

U.S. Pat. No. 5,783,520 describes a process for preparing an encapsulated clomazone formulation. The process involves a step of providing a water immiscible liquid phase consisting of clomazone and polymethylene polyphenyl isocyanate (PMPPI), with edible oils, such as soy bean oil, corn oil, sunflower oil, as a high boiling organic solvent. U.S. Pat. No. 5,783,520 describes the microencapsulation of clomazone by preparing a water-immiscible phase containing specified amounts of clomazone and PMPPI, together with an edible oil. The formulation is alleged to reduce the volatility of clomazone in the completed formulation.

More recently, US 2014/0031231 discloses a wide range of different formulations of clomazone, with microencapsulated formulations being one of the many suggested. A wide range of organic solvents, including but not limited to a range of animal or vegetable oils, for clomazone is suggested. Linseed oil is specifically exemplified in US 2014/0031231 as a solvent for clomazone.

There is a need for an improved clomazone formulation, in particular an improved microencapsulated clomazone formulation.

SUMMARY

Surprisingly, it has been found that particularly effective microencapsulated formulations of clomazone may be prepared using one or more non-edible oils as solvents. In particular, it has been found that the use of non-edible oils provides the clomazone with a high dispersability, while still allowing the formulation to be readily suspended in water during the process for forming the microcapsules. Further, the formulation exhibits a low wet sieve residue that is a high degree of retention of the clomazone active ingredient in the microcapsules. It has also been found that the non-edible oils exhibit a lower toxicity than solvents used in the prior art formulations, in particular the 1,2-benzenedicarboxylic di-($C_3$-$C_6$) branched alkyl esters and the aromatic hydrocarbon and petroleum solvents of the prior art compositions and described above.

Accordingly, in a first aspect, the present invention provides a herbicidal composition comprising an aqueous suspension of microcapsules, the microcapsules having a capsule wall of a porous condensate polymer, wherein the microcapsules contain a solution of clomazone in a solvent system comprising one or more non-edible oils.

Surprisingly, it has been found that microencapsulating clomazone in a solvent system comprising one or more non-edible oils provides a significantly improved formulation, in particular having the properties of a high dispersibility, ease of forming and maintaining in suspension, and a low wet sieve residue. A further advantage is that the non-edible oils used as solvents for the clomazone are significantly less toxic than the solvents known and used in the prior art formulations. Still further, the non-edible oils used in the formulations of the present invention are available at lower costs than the edible oils suggested in the prior art and use of the non-edible oils does not remove valuable oils from the human food chain.

In particular, it has been found that the use of non-edible oils provides clomazone with an enhanced bioactivity. Many non-edible oils are used for insecticidal and fungicidal applications. It has surprisingly been found that dissolving clomazone in non-edible oil gives rise to a significant synergistic effect, while edible oils such as soy bean oil, corn oil, sunflower oil and linseed oil used in the prior art function simply as liquid carriers and are inert to the finished formulation.

DETAILED DESCRIPTION OF EXAMPLE EMBODIMENTS

The clomazone formulation of the present invention comprises microcapsules suspended in an aqueous phase. The microcapsules contain a solution of clomazone in a solvent phase comprising one or more non-edible oils, such that the clomazone in the formulation is retained within the microcapsules.

Clomazone is the common name of 2-[(2-chlorophenyl)methyl]-4,4-dimethyl-3-isoxazolidinone, a compound known to be herbicidally active and commercially available. The formulation of the present invention may comprise clomazone as the sole herbicidally active ingredient. Alternatively, one or more further active ingredients may be present in the formulation, either within the microcapsules and/or within the aqueous phase.

The formulation may comprise clomazone in any suitable amount to provide the required level of activity, when applied to a locus for the control of plant growth. Preferably, the formulation contains clomazone in an amount of at least 10% by weight, more preferably at least 20%, still more preferably at least 40%. Formulations having at least 50% by weight clomazone are also envisaged in the present invention.

In the formulation of the present invention, clomazone is retained in solution in an organic solvent system within the microcapsules. The solvent comprises one or more non-edible oils. Other solvents may be present within the microcapsules. However, it is preferred that the solvent consists essentially of one or more non-edible oils.

The non-edible oils are not soluble in or miscible with water and form an organic phase in the method of preparing the microcapsules, as described hereinbelow.

Non-edible oils are known in the art and are commercially available. References herein to non-edible oils are to vegetable oils, essential oils, mineral oils and fatty acid esters that are not generally considered to be edible by humans.

Suitable vegetable oils, in particular pressed vegetable oil, are all vegetable oils that are non-edible. Such oils can be obtained from plants and examples include Amur cork tree fruit oil, Burdock oil (Bur oil), Candlenut oil (Kukui nut oil), Carrot seed oil (pressed), Castor oil, Imoogra oil, Jojoba oil, Neem oil, Rose hip seed oil, Sea buckthorn oil, Snowball seed oil (Viburnum oil), Tamanu or foraha oil, Tonka bean oil. Castor oil and Neem oil are particularly preferred non-edible oils.

Suitable essential oils are also known and are commercially available. Suitable essential oils include sesame oil, pyrethrum, glycerol-derived lipids or glycerol fatty acid derivatives, cinnamon oil, cedar oil, clove oil, geranium oil, lemon grass oil, angelica oil, peppermint oil, turmeric oil, wintergreen oil, rosemary oil, fennel oil, cardamom oil, caraway oil (caraway oil), chamomile oil, coriander oil, guaiac wood oil, cumin oil, dill oil, parsley oil, basil oil, camphor oil, ylang ylang oil, citronella oil, eucalyptus oil, fennel oil, ginger oil, bitter with Pakistan incense fat (copaiba balsam oil), perilla oil, cedar oil, jasmine oil, rose grass Sofia (palmarosa sofia) oil, western peppermint oil, anise oil (staranisoil), tuberose oil, neroli oil, fat tolu incense, patchouli oil, grass oil, Japanese flat four white oil (Chamaecyparis obtuse oil), Hiba oil, red Tan sandalwood oil, orange leaf oil, bay leaf oil, vetiver oil, bergamot oil, fat Peru incense, rose wood oil (boisderose oil), grapefruit oil, lemon oil, orange oil, orange oil, oregano oil, lavender oil, obtusiloba oil (Lindera oil), pine needle oil, pepper oil, rose oil, orange oil, tangerine oil, tea tree oil, tea oil, thyme oil, thymol oil, garlic oil, onion oil, aloe oil, Japanese peppermint oil, and spearmint oil.

In one embodiment, the oil is an oil from one or more spice plants. In another embodiment, the oil is selected from citronella oil, geranium oil, tea tree oil, lavender oil, Carnation oil (clovepineoil), eucalyptus oil, thyme oil and oregano oil. Pyrethrum oil, citronella oil, and sesame oil are preferred essential oils.

Suitable mineral oils are commercially available and include distillation fractions of petroleum. Preferred mineral oils are mixtures of open-chain $C_{14}$-$C_{30}$ hydrocarbons, closed-chain hydrocarbons (naphthenes) and aromatic hydrocarbons. The hydrocarbons may be linear or branched. Especially preferred mixtures are those with a non-aromatic content of less than 8% by weight, more preferably a non-aromatic content of less than 4% by weight. Examples which may be mentioned here are Exxsol® D140 and white oil.

Suitable fatty acid esters are also known and available commercially. Suitable fatty acid esters may be selected from esters of $C_{10}$ to $C_{20}$ fatty acids, more preferably $C_{12}$ to $C_{20}$ fatty acids, still more preferably $C_{14}$ to $C_{18}$ fatty acids, for example myristates, palmitates, oleates and stearates, and mixtures, such as the cocoates. Examples of suitable fatty acid esters include cetyl alcohol, stearyl alcohol, squalane, isopropyl myristate, isopropyl palmitate, isooctyl palmitate, cetyl palmitate, glyceryl cocoate, glyceryl stearate, glyceryl isostearate, decyl oleate, caprylic/capric acid triglyceride, glyceryl oleate, ethylhexyl palmitate, ethylhexyl stearate, and decyl cocoate. Isooctyl palmitate is a preferred fatty acid ester.

The microcapsules may contain a solution consisting essentially of one or more non-edible oils and clomazone. Other components may be included in the solvent system, as required. Other components that may be present in the solution are known in the art and include surfactants, stabilizers and the like. In particular, antioxidants may be included in the solvent system within the microcapsules. As described in more detail below, preparation of the formulation may require heating of the formulation to cure the polymers walls of the microcapsules. Heating the formulation may increase the rate of oxidation of the active components. Accordingly, one or more antioxidants may be included. Suitable antioxidants are known in the art and are commercially available. Examples include butylated hydroxytoluene (BHT) and butylated hydroxyanisole (BHA). The antioxidant may be present in any suitable amount to reduce or prevent oxidation of the active ingredient and maintain its stability. The amount of antioxidant may be in the range of from 0.005 to 1.0% of the weight of the microcapsules, more preferably from 0.01 to 0.05% by weight.

The size of the microcapsules may be controlled by a number of factors in the preparation of the composition of this invention. In particular, the size of the microcapsules may be controlled by including on or more further components in the water-immiscible liquid phase within the microcapsules, in particular one or more surfactants. The hydrophile-lipophile balance (HLB) of the surfactants employed can influence the size of the microcapsules formed in the composition, with surfactants or surfactant combinations having a lower HLB giving rise to microcapsules having a lower diameter. Suitable oil-soluble surfactants are known and available commercially, for example Atlox 4912, an A-B-A block copolymer surfactant having a low HLB of about 5.5. Other block copolymer surfactants may be used, in particular those composed of polyglycol, for example polypropylenglycol, and hydroxylated polyfatty acids. The surfactants may be present in any suitable amount to impart the required particle size to the microcapsules during preparing of the composition. A preferred concentration in the water-immiscible phase is from 1 to 30%, more preferably about 5 to 25% by weight of the microcapsules.

The non-edible oil solvent system within the microcapsules contains the solvent, in particular the one or more non-edible oils, in sufficient amount to dissolve the required amount of clomazone. Preferably, the weight ratio of clomazone to non-edible oil solvent is from 1:12 to 12:1, more preferably from 1:10 to 10:1, still more preferably from 1:7.5 to 7.5:1.

The liquid phase within the microcapsules preferably contains at least 20% by weight clomazone, more preferably at least 30%, still more preferably at least 50% by weight clomazone. Clomazone may be present in the encapsulated material in an amount of from 1% to 95% by weight, more preferably from 1% to 90%, still more preferably from 5% to 90% by weight.

The non-edible oil solvent is preferably present in the liquid within the microcapsules in an amount of at least 5% by weight, more preferably at least 10% by weight.

The solution of clomazone in the non-edible oil solvent system is contained within the microcapsules. The microcapsules may be formed from any suitable polymer. The polymer of the microcapsules is porous, thereby allowing for the controlled release of the clomazone active ingredient from within the microcapsules. The rate of release of the active ingredient from the microcapsules may be controlled in known manner, for example by the appropriate selection of the polymers used to prepare the microcapsules, selection of the size of the microcapsules, the porosity of the polymer, and the presence of components within the microcapsules. Suitable polymer systems for use in the microencapsulation formulation of the present invention are known in the art. The polymer forming the wall of the microcapsules is preferably formed by interfacial polymerization. Examples of suitable polymers to form the microcapsules include porous condensate polymers of one or more of a polyurea, polyamide or amide-urea copolymer.

Polyureas are preferred polymers for the microcapsules. Polyureas may be formed by the interfacial polymerization of an isocyanate, in particular a polyfunctional isocyanate.

The polyisocyanates used as starting components according to the invention may be aliphatic or aromatic polyisocyanates. For example, aromatic polyisocyanates can be 1,3- and/or 1,4-phenylene diisocyanates, 2,4-, 2,6-tolylene diisocyanates (TDI), crude TDI, 2,4'-, 4,4'-diphenyl methane diisocyanate (MDI), crude MDI, 4,4'-diisocyanatebiphenyl, 3,3'-dimethyl-4-4'-diisocyanate biphenyl, 3,3'-dimethyl-4, 4'diisocyanate diphenylmethane, naphthylene-1,5-diisocyanate, triphenylmethane-4,4',4''-triisocyanate, m- and p-isocyanate phenylsulfonyl isocyanate, polyaryl polyisocyanate (PAPI), diphenylmethane-4,4'-diisocyanate (PMDI), polymethylene polyphenyl isocyanates (PMPPI) and derivatives and prepolymers of aromatic isocyanates.

Aliphatic polyisocyanates can be ethylene diisocyanate, hexamethylene diisocyanate (HDI), tetramethylene diisocyanate, dodecamethylene diisocyanate, 1,6,11-undecan triisocyanate, 2,2,4-trimethylhexa-methylene diisocyanate, lysine diisocyanate, 2,6-diisocyanate methyl caproate, bis (2-isocyanate ethyl)fumarate, bis(2-isocyanate ethyl)carbonate, 2-isocyanate ethyl-2,6-diisocyanate hexanoate, trimethylhexamethylene diisocyanate (TMDI), dimer acid diisocyanate (DDI), isophorone diisocyanate (IPDI), dicyclohexyl diisocyanate, dicyclohexylmethane diisocyanate (H-MDI), cyclohexylene diisocyanate, hydrogenated tolylenediisocyanate (HTDI), bis(2-isocyanate ethyl)-4-cyclohexene-1,2-dicarboxylate, 2,5- and/or 2,6 norbornane diisocyanate, araliphatic polyisocyanates having 8 to 15 carbon atoms, m- and/or p-xylylene diisocyanate (XDI), alpha-, alpha-, alpha-, alpha-tetramethyl xylylene diisocyanate (TMXDI), ethylene diisocyanate hexamethylene diisocyanate, (HDI), tetramethylene diisocyanate, dodecamethylene diisocyanate, 1,6,11-undecan triisocyanate, 2,2,4-trimethylhexamethylene diisocyanate, lysine, diisocyanate, 2,6-diisocyanate methyl caproate, bis(2-isocyanate ethyl)fumarate, bis(2-isocyanate ethyl)carbonate, 2-isocyanate ethyl-2,6-diisocyanate hexanoate, trimethylhexamethylene diisocyanate (TMDI), dimer acid diisocyanate (DDI) and derivatives and prepolymers of aliphatic isocyanates.

The distillation residues obtained from the commercial production of isocyanates which contain isocyanate groups may also be used, optionally as solutions in one or more of the above mentioned polyisocyanates. Any mixtures of the above mentioned polyisocyanates may also be used.

Preferred isocyanates for forming the polyureas are known in the art and are commercially available, including alpha-, alpha-, alpha-, alpha-tetramethyl xylylene diisocyanate (TMXDI), hexamethylene diisocyanate (HDI), HDI derivative (HDI Trimer, HDI Uretdione) which are commercially available Desmodur® N3600, XP2410 and N3400, isophorone diisocyanate (IPDI), polymethylene polyphenyl isocyanates (PMPPI), methylene diphenyl isocyanate (MDI), polyaryl polyisocyanate (PAPI), and toluene diisocyanate (TDI).

The microcapsules of the present invention may be further formed from a polyfunctional amine. Suitable amines for use have two or amine groups. Examples of suitable amines for use in the present invention are diamine and higher polyamine reactants, including ethylene diamine, phenylene diamine, toluene diamine, hexamethylene diamine, diethylene triamine, piperazine, 1,3,5-benzenetriamine trihydrochloride, 2,4,6-triaminotoluene trihydrochloride, tetraethylene pentamine, pentaethylene hexamine, polyethylene imine, 1,3,6-triaminonaphthlene, 3,4,5-triamino-1,2,4-triazole, melamine, and 1,4,5,8-tetraminoanthraquinone.

Preferred amines for forming the polyureas are known in the art and are commercially available, including ethylenediamine (EDA), diethyltriamine (DETA), triethylenetetramine (TETA), and 1,6-hexanediamine (HDA).

As noted above, the size of the microcapsules may be selected to provide the required properties of the formulation, in particular the rate of release of the clomazone active ingredient from the microcapsules. The microcapsules may have a particle size in the range of from 0.5 to 60 microns, more preferably from 1 to 60 microns, still more preferably from 1 to 50 microns. A particle size range of from 1 to 40 microns, more preferably from 1 to 30 microns has been found to be particularly suitable.

The microcapsules may comprise the polymer in a suitable amount to provide the required properties of the formulation. Preferably, the polymer is present in an amount of from 2% to 25% by weight of the microcapsules, more preferably from 3 to 20%, still more preferably from 5 to 15% by weight. A particularly suitable amount of polymer in the microcapsules is in the range of from 5 to 12% by weight.

The formulation of the first aspect of the present invention may comprise the microcapsules as described above suspended in an aqueous phase. The aqueous phase comprises water, together with other components required to impart the desired properties to the formulation, for example stability of the suspension and dispersibility of the microcapsules. Suitable components for inclusion in the aqueous phase of the formulation are known in the art and are commercially available. Suitable components are those that improve and maintain the dispersibility and suspension of the microcapsules, and include one or more surfactants, stabilizers, emulsifiers, viscosity modifiers, protective colloids, and the like.

The aqueous phase may make up any suitable amount of the formulation, provided the microcapsules are well dispersed and maintained in suspension. Typically, the aqueous phase will comprise from 15 to 50% by weight of the formulation, more preferably from 20 to 40%, still more preferably from 25 to 30%.

The formulation of the present invention may be used in known manner to control the growth of plants. In particular, the formulation may be diluted with water to the required concentration of active ingredient and applied to a locus in known manner, such as by spraying.

It has also been found that the formulation of the present invention may be prepared in a dried form that is without the microcapsules being suspended in an aqueous phase.

Accordingly, in a further aspect, the present invention provides a herbicidal composition comprising microcapsules, the microcapsules having a capsule wall of a porous condensate polymer, wherein the microcapsules contain clomazone and a solvent comprising one or more non-edible oils.

Details of the microcapsules and their composition are as hereinbefore described.

The formulation of this aspect of the invention, in use, is typically mixed with water to the required level of dilution to form a suspension of microcapsules in an aqueous phase, which may then be used and applied in known manner, as described above.

The formulations of the present invention may be prepared in a manner analogous to the preparation of known microencapsulation formulations. In general, the reactants forming the polymer of the walls of the microcapsules are dispersed between an organic liquid phase and an aqueous liquid phase, such that polymerization takes place at the interface between the two phases. For example, in the case of microcapsules formed from polyurea, the isocyanate, optionally with a cross-linking agent, such as an acetylene carbamide derivative (ACD) cross-linker, is dispersed in the organic non-edible oil solvent system, together with the clomazone active ingredient, while the adjuvant is dispersed in the aqueous phase. The two phases are then mixed, to allow the polymer to form at the interface.

Acetylene carbamide derivatives (ACD) useful as cross-linking agents are known in the art, for example as disclosed in US 2011/0269063. Suitable ACDs are also known as glycoluril resins and include those represented by the following formula:

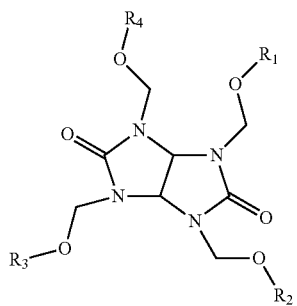

wherein R1, R2, R3, and R4 each independently represents a hydrogen atom or an alkyl with, for example, 1 to about 12 carbon atoms, 1 to about 8 carbon atoms, 1 to about 6 carbon atoms, or with 1 to about 4 carbon atoms.

The glycoluril resin can be water soluble, dispersible, or indispersible. Examples of the glycoluril resin include highly alkylated/alkoxylated, partially alkylated/alkoxylated, or mixed alkylated/alkoxylated, and more specifically, the glycoluril resin can be methylated, n-butylated, or isobutylated. Specific examples of the glycoluril resin include CYMEL® 1170, 1171 and 1172. CYMEL® glycoluril resins are commercially available from CYTEC Industries, Inc.

The normally liquid, substantially fully mixed-alkylated, substantially fully methylolated acetylene carbamides are a class of cross-linking agents, the starting material of which is acetylene carbamide, per se, which is also known as acetylene diurea which is prepared by reacting two moles of urea with one mole of glyoxal. The precise chemical name for acetylene carbamide is tetrahydroimidazo-(4, 5-d) imidazole 2, 5(1H, 3H)-dione. The acetylene carbamide can be fully methylolated by reacting one mole of acetylene carbamide with four moles of formaldehyde. The resulting product is identified as tetramethylol acetylene carbamide. The tetramethylol acetylene carbamide is then reacted with a selected amount of methanol so as to partially methylate the fully methylolated acetylene carbamide which is then followed by alkylation with a higher aliphatic monohydric alcohol containing from two to four carbon atoms. These monohydric alcohols may be primary or secondary alcohols. These higher monohydric aliphatic alcohols containing from two or four carbon atoms may be ethanol, n-propanol, isopropanol, n-butanol, isobutanol and the like. It is sometimes advantageous to fully methylate the tetramethylol acetylene carbamide and then by use of a transetherification reaction incorporate the desired measure of ethanol, propanol or butanol into the acetylene carbamide derivative.

These fully etherified, fully methylolated acetylene carbamide derivatives are not considered to be resinous materials since they are, as individual entities, simple pure compounds or mixtures of simple pure compounds but they are potential resin-forming compounds which enter into chemical reaction with certain ionic water-dispersible, non-gelled polymeric materials when subjected to heat and particularly when subjected to heat under acidic conditions. The concept of the degree of methylation or more broadly alkylation, on average, and the concept of the degree of methylolation, on average, will be discussed herein below in order that this concept may be fully understood.

Theoretically, it is possible to methylolate acetylene carbamide fully, that is, to produce tetramethylol acetylene carbamide. However, frequently, in a commercial composition purporting to be tetramethylol acetylene carbamide, when analyzed, may show a fractional degree of methylolation. It is well recognized that fractional methylolation is not considered to be possible. As a consequence, when a composition contains on analysis a degree of methylolation of 3.70, 3.80, or 3.90, it has to be recognized that this is an average degree of methylolation of the acetylene carbamide compound and establishes logically that the aforementioned methylol composition is composed of a mixture of a preponderant amount of tetramethylol acetylene carbamide with comparatively minor amounts of trimethylol acetylene carbamide and, perhaps, insignificant amounts including traces of such derivatives as dimethylol acetylene carbamide and even monomethylol acetylene carbamide. The same concept of averages is also applicable to the alkylation or etherification of the tetramethylol acetylene carbamide composition. There cannot be, based on present reasoning, a fractional alkylation and, as a consequence, when on analysis, a given composition shows that the degree of methylation is, on average, between about 0.9 and 3.60 and that the higher alkylation has an average degree of ethylation, propylation and/or butylation, on average, correspondingly between about 2.80 and 0.40, it must be concluded that there is present in such a composition a plurality of the mixed ethers of the tetramethylol acetylene carbamide. For example, there may be present some monomethyl ether, triethyl ether of tetramethylol acetylene carbamide, some dimethyl ether, diethyl ether of tetramethylol acetylene carbamide, some trimethyl ether, monoethyl ether of tetramethylol acetylene carbamide. There may even be traces of the tetramethyl ether of tetramethylol acetylene carbamide. There may also be present with the varying methyl ethers of tetramethylol acetylene carbamide varying mono, di and tri ethyl ethers, mono, di and tri propyl ethers and mono, di and tri butyl ethers of tetramethylol acetylene carbamide. It is possible to produce a monomethyl ether, monoethyl ether, monopropyl ether, monobutyl ether of tetramethylol acetylene carbamide which could be classed as a tetramixed-alkylated derivative. It is generally preferred, however, to make use of only one higher monohydric alcohol containing from two to four carbon atoms with the methyl alcohol in making a mixed full ether of the tetramethylol acetylene carbamide. The dimixed-alkylated products are, therefore, preferred, although the trimixed-alkylated derivatives as well as the tetramixed-alkylated derivatives may also be used.

Regarding ACDs preferred are the ACDs of the Powderlink® 1174 and Cymel® type commercial products, more preferably Cymel® 1171 (that is a highly alkylated glycouril resin) and Cymel® 1170 (that is a butylated glycoluril resin). The use of prepolymers of Cymel-type has been found to result in a more irregular reaction course when compared with the use of Powderlink® 1174. Therefore the most preferred ACD is Powderlink® 1174 (that is tetrakis (methyoxymethyl) glycoluril, CAS No. 17464-88-9). It should be noted that the commercial products may have compounds other than the monomers referred in the label (for example, Powderlink® 1174 may contain oligomers).

The selection of the cross-linking agent and the amount present may be used to control the porosity of the polymer wall of the microcapsules. Preferably, the composition comprises the cross-linking agent in an amount of from 0.1 to 20%, more preferably from 0.5 to 15% by weight of the microcapsules.

In a further aspect, the present invention provides a method for preparing a herbicide composition, the method comprising the steps of:

providing a water immiscible phase comprising clomazone, an isocyanate and optionally an ACD cross-linker, dissolved in a solvent system comprising one or more non-edible oils;

providing an aqueous phase comprising one or more surfactants;

combining the water immiscible phase and the aqueous phase to form a dispersion of the water immiscible phase in the aqueous phase;

thereby forming microcapsules of polyurea containing droplets of the water immiscible phase; and curing the microcapsules.

The method comprises combining a water immiscible phase and an aqueous phase. This is carried out under conditions, such as with agitation, to form a dispersion of the water immiscible phase in the aqueous phase.

The aqueous phase contains at least one surfactant or emulsifier, to assist in forming the dispersion of the water immiscible phase in the aqueous phase. Other components required to impart the desired properties to the final composition, as noted above, may be included in the aqueous phase.

The microcapsules are formed by interfacial polymerization reactions of the isocyanate, and then cross-linked by the ACD resin. The polymerization reaction is preferably allowed to proceed while the dispersion is being agitated. The microcapsules once formed are cured, preferably by heating, to harden the polymer walls of the microcapsules. Curing typically takes place at a temperature of from 30 to 60° C., more preferably from 40 to 50° C., for a suitable length of time, typically from 1 to 5 hours, more typically from about 2 to 4 hours.

The resulting composition is preferably then filtered, after cooling, to provide a suspension of the microcapsules in the aqueous phase. The resulting product is a CS formulation of clomazone suitable for use and application as described above, in particular by dilution with water and application by spraying. Should it be required to prepare dry microcapsules, the resulting composition is subject to a drying stage, to remove the aqueous phase. Any suitable drying techniques may be employed, with spray drying being particularly effective.

The composition may be prepared with microcapsules formed from other polymers, as noted hereinbefore, using the appropriate wall-forming reagents in an analogous manner to the above procedure.

In a further aspect, the present invention provides the use of a clomazone formulation as hereinbefore described in the control of plant growth.

In a still further aspect, the present invention provides a method of controlling plant growth at a locus, the method comprising applying to the locus a formulation of microencapsulated clomazone as hereinbefore described.

Embodiments of the present invention will now be described, for illustration only, by way of the following examples.

Example 1

Preparation of Microencapsulated Clomazone with Castor Oil

A water immiscible phase and an aqueous phase were prepared having the following composition (with amounts of the components expressed in % weight of the final composition):
A. A water-immiscible organic phase, prepared just prior to use, had the following composition:
  9.36 g technical clomazone
  0.77 g. polymethylene polyphenylisocyanate (PMPPI, Suprasec-5005)
  1.47 g Castor oil
B. An aqueous solution was prepared having the following composition:
  1.60 g POE (20) sorbitan trioleate
  0.16 g Lignosulfonic acid, sodium salt (Kraftsperse 25M)
  0.16 g Sulfonated aromatic polymer, sodium salt (MORWET D-425 POWDER)
  0.03 g Antiforam (Dow Corning® 1500)
  6.18 g Water
Step 1
  0.77 g isocyanate (Suprasec-5005) was dispersed in 1.47 g castor oil. The resulting combination was mixed well at high speed in a high-shear mixer and was stirred for 10 min. 9.36 g clomazone was finally added to form the organic phase.
Step 2
  1.60 g POE (20) sorbitan trioleate, 0.16 g lignosulfonic acid, sodium salt (Kraftsperse 25M), 0.16 g sulfonated aromatic polymer, sodium salt (MORWET D-425 POWDER) and 0.03 g antifoam (Dow Corning®1500) was added in 6.18 g water to form the aqueous phase.
Step 3
  The water-immiscible organic phase was added dropwise into the aqueous phase. After mixing by high-shear mixer, an oil-in-water dispersion was formed.
Step 4
  The oil-in-water dispersion was transfer into a Erlenmeyer flask. 0.77 g diethylenetriamine aqueous solution (0.77 g diethylenetriamine in 1.73 g water) was added dropwise with stirring. The dispersion was heated and maintained at about 50° C. for 4 hrs. The resulting mixture was then allowed to cool. Adjuvants, such as stabilizers (1.69 g calcium chloride, 0.70 g sodium nitrate), thickening agent (2% Xanthan gum, 0.67 g), antifreeze agent (1.60 g propylene glycol) were added when the temperature was cooled down to about 30° C. The pH was adjusted by addition of a pH adjuster (hydrochloric acid 36-38%) to a pH in the range of from 6 to 9.

Examples 2 to 13 and Comparative Examples

The procedure of Example 1 was repeated for a range of different solvent systems for clomazone comprising non-edible oils, as indicated in Table 1 below. For comparison purposes, the procedure of Example 1 was repeated using a range of edible oils as solvents, in particular corn oil, soybean oil and sunflower oil, again as indicated in Table 1 below.

Volatility Studies

Laboratory tests to determine the volatility of clomazone formulated in a capsule suspension (CS) formulation were carried out in the following manner.

Sufficient unsterilized topsoil to conduct the test was passed twice through a 14-mesh sieve to remove large particles and debris. The fine particles were then removed through a 30-mesh sieve, leaving behind topsoil of intermediate-sized particles. This intermediate-sized topsoil, 240 grams, was spread uniformly to a thickness of about one to two millimeters over an area of about 27.9 cm.×41.3 cm in a tray measuring 32.4 cm×45.7×1.9 cm. The topsoil was then sprayed from an overhead track sprayer calibrated to deliver 20 gallons of water per acre. The spray mix consisted of sufficient clomazone test formulation to provide 0.0712 gm of active ingredient in 20 mL of water. In this manner the clomazone test formulation was applied to the soil at a rate of 1.0 kg active ingredient/ha. Immediately after treatment, the soil was enclosed in a glass jar, where it remained briefly until used.

For each clomazone test formulation, four 22 mm×300 mm glass chromatography columns, each containing a coarse sintered glass barrier at the bottom, were connected through their bottom ends to a multi-port air manifold, which delivered equal air pressure simultaneously to a number of columns. In each of the four columns was placed 59 g of the treated topsoil, which filled about 200 mm of the column length. In the top of each column was then placed a polyurethane foam plug designed to fit inside a 21 to 26 mm diameter tube. As soon after the soil treatment and the columns could be set up, a slow stream of air (0.75-1.00 liter per minute per column) from the multi-port air manifold was passed through the soil in each column, causing the volatilized clomazone to collect on the polyurethane foam plug. The time between the soil treatment and the start of the air flow was about one hour. The air flow was continued for about 18 hours.

Following the 18 hour collection period, the polyurethane foam plug from each column was placed in a 20 mL plastic syringe. The polyurethane foam plug was thoroughly extracted by drawing 15 mL of methanol into the syringe and through the plug, forcing the methanol extract into a beaker, and repeating the process several times. A 0.04 mL aliquot of the 15 mL sample was diluted with 0.96 mL of methanol and 1.0 mL of water. A 0.1 mL aliquot of this solution was analyzed for clomazone content using an enzyme-linked immunosorbent assay (ELISA), a method reported by R. V. Darger et al. (J. Agr. and Food Chem., 1991, 39, 813-819). The total clomazone content of the foam plug, expressed in micrograms (μg), of each sample was recorded.

The results are set out in Table 1 below.

TABLE 1

| Example | Solvent | Amount of clomazone collected (μg) |
|---|---|---|
| Comparative Examples | | |
| A | Corn oil | 20 |
| B | Soybean | 23 |
| C | Sunflower | 21 |
| Vegetable Oil | | |
| 1 | Castor oil | 19 |
| 2 | Neem Oil | 20 |
| Essential Oil | | |
| 3 | Citronella oil | 23 |
| 4 | Pyrethrum oil | 20 |
| 5 | Geranium | 19 |
| 6 | Sesame oil | 21 |
| 7 | Tea tree oil | 24 |
| 8 | Clove oil | 20 |
| 9 | Cotton seed oil | 23 |
| 10 | Ginger oil | 22 |
| Mineral Oil | | |
| 11 | Exsol ® D140 | 23 |
| 12 | White oil | 20 |
| Fatty acid esters | | |
| 13 | Isooctyl palmitate | 22 |

As can be seen from the results set out in Table 1, the formulations of the present invention exhibited a clomazone volatility either the same or less than the comparative formulations employing a solvent system comprising an edible oil.

Efficacy Studies

The biological efficacy of the products of Examples 1 to 13 was compared with clomazone content of the sample of the comparative formulation B, that is clomazone in a solvent system of soybean oil, using the following procedure:

Seeds of barnyard grass, giant foxtail, green foxtail, shatter-cane, and velvetleaf were planted in a 25 cm×15 cm×7.5 cm fiber flat containing topsoil. Each species was planted as a single row in the flat, which contained five rows. There were four replicate flats of the aforementioned weed species for each rate of application of the formulation being tested.

Stock solutions of each of the formulations being tested were prepared by dispersing a sufficient amount of formulation to provide 0.0356 grams of active ingredient in 40 mL of water. From the stock solution 20 mL was removed and serially diluted with 20 mL of water to provide application rates of 0.5, 0.25, 0.125, 0.0625 and 0.0313 g active ingredient/ha. The solutions of test formulation for each rate of application were then sprayed onto the surface of the soil using a track-sprayer and a spray hood.

Flats were also sprayed as above with the same rates of the comparative Formulation B (clomazone with soybean oil).

Upon completion of the spraying, the flats were placed in a greenhouse, where they were maintained for fourteen days. After this time, the test was visually evaluated for percent weed control. The percent weed control data for each formulation being tested and the comparative clomazone in soybean oil formulation was subjected to regression analysis to determine the rate of application that would provide 85% weed control ($ED_{85}$) of each of the weed species. From these data the relative potency of the test formulation (the relative potency of the comparative clomazone in soybean oil, Formulation B, being 1.0) was determined using the following ratio:

$$\text{Relative Potency of Formulation} = \frac{\text{Potency of Example } (ED_{85})}{\text{Potency of Formulation } B \ (ED_{85})}$$

The efficacy of both the formulation of Example 1 and comparative Formulation B above with respect to Barnyardgrass was determined as follows:

The results of the field study of the effects of Formulation B and Example 1 on the control of Barnyardgrass are set out in Table 2 below.

TABLE 2

| Application rate of | Percent Control of Barnyardgrass | |
|---|---|---|
| Clomazone (g/ha) | Formulation B | Example 1 |
| 0.0313 | 70 | 80 |
| 0.0625 | 75 | 90 |
| 0.125 | 91 | 95 |
| 0.25 | 98 | 97 |
| 0.5 | 100 | 100 |

The application rate of clomazone necessary to achieve a control of Barnyardgrass of 85% ($ED_{85}$) was determined from the data contained in Table 2. The potency of each formulation was determined as being the reciprocal of the application rate. The results are set out in Table 3 below.

TABLE 3

| | Application rate to achieve 85% control rate (g/ha) | Potency (ha/g) |
|---|---|---|
| Formulation B | 0.107 | 1/0.107 = 9.3458 |
| Example 1 | 0.042 | 1/0.042 = 23.80 |

The relative potency of the formulation of Example 1 is calculated as follows:

Relative potency of Example 1=23.80/9.3458=2.5

A relative potency of greater than 1 indicates a potency that is higher than the comparative Formulation B.

The results are set out in Table 4 below.

TABLE 4

| | Formulation Relative Potency | | | | |
|---|---|---|---|---|---|
| Example | Barnyard grass | Giant foxtail | Green foxtail | Shatter-cane | Velvetleaf |
| 1 | 2.5 | 3 | 2.7 | 2.5 | 3 |
| 2 | 3.1 | 2.9 | 2.9 | 3.0 | 3 |
| 3 | 1.9 | 2.3 | 2 | 1.8 | 2 |
| 4 | 3 | 2.6 | 2.8 | 3 | 3.5 |
| 5 | 2.9 | 2.5 | 3 | 3.2 | 2.7 |
| 6 | 3.9 | 4 | 3.5 | 4.2 | 3.1 |
| 7 | 2.8 | 2.7 | 3.1 | 3 | 3.2 |
| 8 | 3.2 | 3.5 | 3.2 | 3 | 3.3 |
| 9 | 3 | 2.9 | 2.7 | 3 | 3 |
| 10 | 1.9 | 1.7 | 1.9 | 2.1 | 2 |
| 11 | 2.8 | 2.7 | 3 | 2.7 | 3.1 |
| 12 | 3.2 | 2.9 | 3 | 3.2 | 3 |
| 13 | 2.9 | 3 | 2.7 | 3.1 | 2.8 |
| Formulation B (clomazone in soybean oil) | 1 | 1 | 1 | 1 | 1 |

From the data set out Table 4 above, it can be seen that the formulations of the Examples of the present invention exhibit significantly improved herbicidal activity compared to that of Formulation B.

The invention claimed is:

1. A herbicidal composition comprising an aqueous suspension of microcapsules, the microcapsules having a capsule wall of a porous condensate polymer, wherein the microcapsules contain a solution of clomazone in a solvent system comprising one or more oils, wherein the oil is selected from the group consisting of Neem oil, Pyrethrum oil, Sesame oil, and Clove oil, and wherein the walls of the microcapsules are formed from a polyurea formed by the interfacial polymerization of an isocyanate and optionally an ACD cross-linking agent.

2. The composition according to claim 1, wherein clomazone is present in the composition in an amount of at least 20% by weight.

3. The composition according to claim 2, wherein clomazone is present in the composition in an amount of at least 50% by weight.

4. The composition according to claim 1, wherein the solvent system consists essentially of one or more oils.

5. The composition according to claim 1, wherein the microcapsules further contain one or more surfactants, stabilizers or a mixture thereof.

6. The composition according to claim 1, wherein the weight ratio of clomazone to the oil is from 1:12 to 12:1.

7. The composition according to claim 6, wherein the weight ratio of clomazone to the oil is from 1:10 to 10:1.

8. The composition according to claim 7, wherein the weight ratio of clomazone to the oil is from 1:7.5 to 7.5:1.

9. The composition according to claim 1, wherein the solution of clomazone in a solvent system within the microcapsules contains at least 20% by weight clomazone.

10. The composition according to claim 1, wherein the solution of clomazone in a solvent system within the microcapsules contains at least 30% by weight clomazone.

11. The composition according to claim 1, wherein the solution of clomazone in a solvent system within the microcapsules contains at least 50% by weight clomazone.

12. The composition according to claim 1, wherein clomazone is present in the encapsulated solution of clomazone in a solvent system in an amount of from 1% to 95% by weight.

13. The composition according to claim 1, wherein clomazone is present in the encapsulated solution of clomazone in a solvent system in an amount of from 5% to 90% by weight.

14. The composition according to claim 1, wherein the oil is present in the solution of clomazone in a solvent system within the microcapsules in an amount of at least 5% by weight.

15. The composition according to claim 14, wherein the oil is present in the solution of clomazone in a solvent system within the microcapsules in an amount of at least 10% by weight.

16. The composition according to claim 1, wherein the isocyanate is selected from the group consisting of alpha-, alpha-, alpha-, alpha-tetramethyl xylene diisocyanate (TMXDI), hexamethylene diisocyanate (HDI), isophorone diisocyanate (IPDI), polymethylene polyphenyl isocyanates (PMPPI), methylene diphenyl isocyanate (MDI), polyaryl polyisocyanate (PAPI), and toluene diisocyanate (TDI).

17. The composition according to claim 1, wherein the ACD crosslinker is selected from the group consisting of tetrakis (methyoxymethyl) glycoluril and an alkylated glycoluril resin.

18. The composition according to claim 1, wherein the microcapsules have a particle size in the range of from 0.5 to 60 microns.

19. The composition according to claim 18, wherein the microcapsules have a particle size in the range of from 1 to 50 microns.

20. The composition according to claim 19, wherein the microcapsules have a particle size in the range of from 1 to 30 microns.

21. The composition according to claim 1, wherein the polymer is present in the microcapsules in an amount from 2% to 25% by weight of the microcapsules.

22. The composition according to claim 21, wherein the polymer is present in the microcapsules in an amount of from 5 to 15% by weight.

23. The composition according to claim 1, wherein the aqueous phase comprises one or more surfactants, stabilizers, viscosity modifiers, or protective colloids.

24. The composition according to claim 1, wherein the aqueous phase comprises from 15 to 50% by weight of the formulation.

25. The composition according to claim 1, wherein the oil is selected from the group consisting of Sesame oil and Clove oil.

26. A method of controlling plant growth at a locus, the method comprising applying to the locus a composition according to claim 1.

27. A herbicidal composition comprising microcapsules, the microcapsules having a capsule wall of a porous condensate polymer, wherein the microcapsules contain clomazone and a solvent comprising an oil, wherein the oil is selected from the group consisting of Neem oil, Pyrethrum oil, Sesame oil, and Clove oil, and wherein the walls of the microcapsules are formed from a polyurea formed by the interfacial polymerization of an isocyanate and optionally an ACD cross-linking agent.

28. A method for preparing a herbicidal composition, the method comprising the steps of:
  providing a water immiscible phase comprising clomazone, an isocyanate and optionally an ACD cross-linker, dissolved in a solvent system comprising an oil, wherein the oil is selected from the group consisting of Neem oil, Pyrethrum oil, Sesame oil, and Clove oil;

providing an aqueous phase comprising one or more surfactants;

combining the water immiscible phase and the aqueous phase to form a dispersion of the water immiscible phase in the aqueous phase;

thereby forming microcapsules of polyurea formed by the interfacial polymerization of an isocyanate and optionally an ACD cross-linking agent and containing droplets of the water immiscible phase; and curing the microcapsules.

29. The method according to claim 28, further comprising drying the resulting composition to remove the aqueous phase.

* * * * *